US009339442B2

(12) United States Patent
Tai et al.

(10) Patent No.: US 9,339,442 B2
(45) Date of Patent: May 17, 2016

(54) MULTI-BALLOON DILATION DEVICE FOR PLACING CATHETER TUBES

(75) Inventors: Kok-Ming Tai, Lawrenceville, GA (US); Donald J. McMichael, Roswell, GA (US); John A. Rotella, Roswell, GA (US); Nathan C. Griffith, Roswell, GA (US); Emily A. Reichart, Atlanta, GA (US); Courtney E. Rowe, Marietta, GA (US); Steven A. Holley, Cumming, GA (US); Edward B. Madsen, Cumming, GA (US)

(73) Assignee: Avent, Inc., Alpharetta, GA (US)

( * ) Notice: Subject to any disclaimer, the term of this patent is extended or adjusted under 35 U.S.C. 154(b) by 0 days.

(21) Appl. No.: 13/245,562

(22) Filed: Sep. 26, 2011

(65) Prior Publication Data

US 2012/0078176 A1    Mar. 29, 2012

Related U.S. Application Data

(60) Provisional application No. 61/386,793, filed on Sep. 27, 2010, provisional application No. 61/446,229, filed on Feb. 24, 2011.

(51) Int. Cl.
*A61M 31/00*    (2006.01)
*A61J 15/00*    (2006.01)
(Continued)

(52) U.S. Cl.
CPC ......... *A61J 15/0015* (2013.01); *A61B 17/3415* (2013.01); *A61J 15/0038* (2013.01); *A61J 15/0042* (2013.01); *A61M 25/1002* (2013.01); *A61M 25/1011* (2013.01); *A61M 29/02* (2013.01); *A61M 2025/1013* (2013.01)

(58) Field of Classification Search
CPC ............... A61M 25/1002; A61M 25/1011; A61M 2025/1015; A61M 2025/1065; A61M 2025/1013; A61J 15/0015; A61J 15/0042; A61J 15/0034; A61J 15/0053; A61J 15/0049
USPC ............ 604/101.01, 101.05, 103.05, 164.03, 604/164.04
See application file for complete search history.

(56) References Cited

U.S. PATENT DOCUMENTS 4,763,654 A * 8/1988 Jang .................. A61M 25/1011
604/101.01
5,112,310 A    5/1992 Grobe
(Continued)

FOREIGN PATENT DOCUMENTS

WO    WO 02/19890 A2    3/2002
WO    WO 2008/154533 A1    12/2008
WO    WO 2011/159590 A2    12/2011

OTHER PUBLICATIONS

Co-pending U.S. Appl. No. 13/245.577, filed Sep. 26, 2011, by Tai et al. for "Dilation Device for Placing Catheter Tubes."

*Primary Examiner* — Emily Schmidt
(74) *Attorney, Agent, or Firm* — Dority & Manning, P.A.

(57) ABSTRACT

A stoma dilation device that includes a tubular support defining a continuous pathway through the device; at least one inflatable dilation balloon and at least one inflatable retention balloon located on the tubular support; and inflation lumens for each balloon. The inflatable dilation balloon forms at least a first portion of the device and the inflatable retention balloon forms at least a second portion of the device. The inflatable retention balloon is configured to have a diameter upon full, unrestrained inflation that is greater than the largest diameter of the inflatable dilation balloon upon inflation.

19 Claims, 4 Drawing Sheets

(51) Int. Cl.
*A61M 25/10* (2013.01)
*A61B 17/34* (2006.01)
*A61M 29/02* (2006.01)

(56) References Cited

U.S. PATENT DOCUMENTS

| | | | |
|---|---|---|---|
| 5,458,583 A | 10/1995 | McNeely et al. | |
| 5,505,698 A * | 4/1996 | Booth | A61M 25/1002 604/103.11 |
| 6,019,746 A | 2/2000 | Picha et al. | |
| 6,236,879 B1 | 5/2001 | Konings | |
| 6,293,924 B1 * | 9/2001 | Bagaoisan | A61M 25/1011 604/103.07 |
| 6,464,686 B1 * | 10/2002 | O'Hara | A61B 17/3415 604/256 |
| 7,220,252 B2 | 5/2007 | Shah | A61M 25/1011 604/101.02 |
| 7,273,056 B2 | 9/2007 | Wilson et al. | |
| 7,396,354 B2 | 7/2008 | Rychnovsky et al. | |
| 7,708,716 B2 * | 5/2010 | Shah | A61M 25/1011 604/101.02 |
| 7,757,695 B2 | 7/2010 | Wilson et al. | |
| 8,414,611 B2 * | 4/2013 | Chalekian | A61F 2/954 606/192 |
| 9,108,024 B2 * | 8/2015 | Tai | A61J 15/0042 |
| 2003/0100909 A1 | 5/2003 | Suzuki | |
| 2003/0225312 A1 | 12/2003 | Suzuki et al. | |
| 2006/0095066 A1 * | 5/2006 | Chang et al. | 606/199 |
| 2007/0203445 A1 * | 8/2007 | Kaye | A61M 1/3653 604/6.16 |
| 2007/0225677 A1 * | 9/2007 | Rowe et al. | 604/509 |
| 2008/0109056 A1 * | 5/2008 | Chalekian | A61F 2/954 623/1.11 |
| 2008/0194973 A1 | 8/2008 | Imam | |
| 2008/0228066 A1 | 9/2008 | Waitzman | |
| 2008/0287983 A1 | 11/2008 | Smith et al. | |
| 2009/0281379 A1 | 11/2009 | Binmoeller et al. | |
| 2009/0318757 A1 | 12/2009 | Singh | |
| 2009/0318798 A1 | 12/2009 | Singh et al. | |
| 2010/0081991 A1 * | 4/2010 | Swisher | A61J 15/0042 604/101.05 |
| 2010/0087706 A1 | 4/2010 | Syed et al. | |
| 2010/0198005 A1 * | 8/2010 | Fox | 600/104 |

* cited by examiner

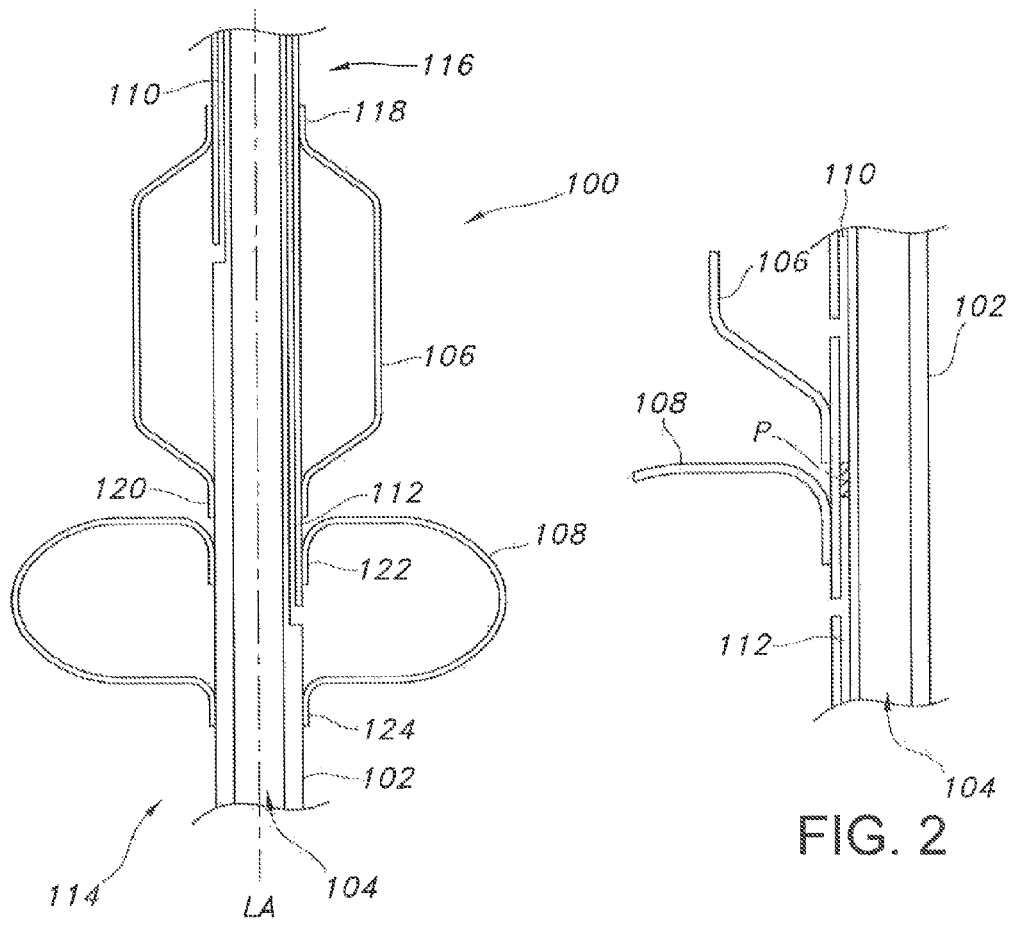

MULTI-BALLOON DILATION DEVICE FOR PLACING CATHETER TUBES

This application claims the benefit of priority from U.S. Provisional Application No. 61/386,793 filed on Sep. 27, 2010 and U.S. Provisional Application No. 61/446,229 filed on Feb. 25, 2011, the contents of which are incorporated herein by reference.

FIELD OF THE INVENTION

The present invention relates to catheters such as feeding tubes and their placement in the body of a patient.

BACKGROUND

Numerous situations exist in which a body cavity needs to be catheterized to achieve a desired medical goal. One relatively common situation is to provide nutritional solutions or medicines directly into the stomach or intestines. A stoma is formed in the stomach or intestinal wall and a catheter is placed through the stoma. This surgical opening and/or the procedure to create the opening is commonly referred to as "gastrostomy". Feeding solutions can be injected through the catheter to provide nutrients directly to the stomach or intestines (known as enteral feeding). A variety of different catheters intended for enteral feeding have been developed over the years, including some having a "low profile" relative to the portion of the catheter which sits on a patient's skin, as well as those having the more traditional or non-low profile configuration. These percutaneous transconduit catheters (sometimes referred to as "percutaneous transconduit tubes") are frequently referred to as "gastrostomy catheters", "percutaneous gastrostomy catheters", "PEG catheters" or "enteral feeding catheters". U.S. Pat. No. 6,019,746 for a "Low Profile Balloon Feeding Device" issued to Picha et al. on Feb. 1, 2000, provides an example of one device.

These catheters are frequently placed in a procedure called percutaneous endoscopic gastrostomy (frequently referred to as PEG). Traditionally, a PEG tube is placed using endoscopic guidance or x-ray guidance. In a conventional PEG procedure that places a PEG tube into a patient's stomach, an endoscope is used to observe that the patient's esophagus is unobstructed and to inspect and inflate the stomach to see that the area selected for the gastrostomy can be distended.

If the location is suitable, this spot is selected. In some types of procedures, prior to placement of any feeding tube, it has been found that it is particularly desirable to anchor the anterior wall of the gastric lumen (e.g., the stomach) to the abdominal wall as a step prior to creating the stoma tract through the two. Thus attachment has been found to be critical as it helps to prevent inadvertent separation and exposure of the peritoneal cavity to contamination and possible peritonitis. This procedure is also applicable to jejunostomy or gastro-jejunostomy as well as the gastrostomy procedure referred to above. Similar procedures may also be applicable or desirably for other catheter tubes such as peritoneal drainage tubes.

After the wall of the lumen is anchored, a needle is inserted into the patient in the area in the appropriate location. Additionally, a small incision may be made in the skin. An endoscopist will then typically watch through the endoscope as a needle pushes through the patient's skin, then through the abdominal wall, and enters the gastric lumen in the selected area to form a needle tract. A guide wire is passed through the needle into the gastric lumen (e.g., the stomach). The endoscopist will use an endoscopic snare to grasp the guide wire firmly. The snare, passed through the working channel of the endoscope, firmly grabs the guide wire. Both the endoscope and snare are then withdrawn together through the patient's mouth, pulling the guide wire with them. The end of the guide wire that extends out from the patient's mouth is subsequently attached to a PEG tube and the other end of the guide wire remains outside the patient's skin in the abdominal region.

The PEG tube is guided into the patient's mouth (while the endoscope is completely removed from the patient) and pulled into the patient's gastric lumen as the guide wire is pulled from the end that remains outside the patient's skin. Once the PEG tube is in the gastric lumen, it is pulled partially through the gastric and abdominal walls until a bumper of the PEG tube is snug against the gastric mucosa. However, in order for the PEG tube to be pulled partially through the gastric and abdominal walls and skin, the original needle tract must be dilated. This dilation is carried out with conventional dilation devices that employ a tapered dilator at the distal end of the PEG tube so that it dilates the opening as it is pulled through the gastric mucosa. During such dilation, the endoscope is again passed into the patient and subsequently used to visually observe that the bumper of the PEG tube is snug against the gastric mucosa.

In other conventional PEG tube placement procedures, endoscopy is not used at all. Instead, x-ray techniques are used to help select a particularly suitable location in the patient's body (e.g., the stomach) for the introduction of the PEG tube. X-ray is used for guiding the PEG tube placement and for inspecting the PEG tube's final position.

There are many problems associated with these conventional procedures including: increased risk of esophageal trauma associated with multiple passes of an endoscope into and out of a patient; placement of the PEG in an improper location, transit of a large catheter tube such as a PEG through the esophagus; and/or additional complications and/or trauma of anchoring the wall of the lumen to the abdomen. While avoiding these problems may be desirable, suitable devices or procedures are lacking.

Accordingly, there is a need for a device, system and method for placing a non-vascular catheter tube such as a PEG tube in a patient that reduces these risks and trauma and is easy to perform.

SUMMARY

In response to the difficulties and problems discussed herein, the present invention provides a dilation device and dilation system. The dilation device is an inflatable device that is used for placing catheter tubes in a non-vascular lumen, desirably under direct visualization using an endoscope. Since the stomach is a common example of a non-vascular lumen, for the purpose of describing the present invention, the use of the term "gastric lumen" or "stomach" is representative of all other non-vascular lumens or spaces (e.g., duodenum, jejunum, ileum, peritoneal cavity, etc.), unless otherwise specified.

According to the invention, a conventional endoscope is advanced into the stomach to insufflate and allow palpation to locate an appropriate site. Once the appropriate site is located, a needle is inserted into the stomach through the abdomen from outside the body to form a needle tract. A guide wire is then introduced into the stomach through the needle, and a system is provided for: positioning a dilation device in the needle tract; maintaining the dilation device in the desired position; dilation of the needle tract, and removal of the dilation device.

The dilation device includes at least an inflatable dilation balloon and an inflatable retention balloon, an inflation lumen to inflate and deflate the dilation balloon, an inflation lumen to inflate and deflate the retention balloon, a tubular support, and a continuous pathway through the device that accommodates a guide wire. The dilation balloon may be compliant, semi-compliant, or non-compliant.

The device may have a distal end and a proximal end. At least one dilation balloon is located towards the distal end of the device. The dilation balloon(s) has a length with a predetermined diameter upon full inflation to fit a specific sized catheter tube device. Alternatively, the dilation balloon(s) may be dilated to various effective diameters using respectively different inflation pressures to fit various catheter tubes. The proximal section of the device (that portion of the dilation device that is positioned in the non-vascular lumen) incorporates at least one retention balloon (also referred to as the "proximal retention balloon") having a substantially larger diameter than any diameters of the dilation balloon(s). Once this retention balloon is inflated, it functions to provide retention of the dilation device within the non-vascular lumen (e.g., the stomach). The proximal retention balloon component may be compliant, semi-compliant, or non-compliant. The dilation balloon and the retention balloon may be formed of the same materials or they may each be formed of a different material. Each balloon desirably includes two opposing open ends. The open ends may be attached to the tubular support.

The tubular support of the dilation device supports the dilation balloon(s) and the retention balloon(s). The dilation device also has at least one inflation lumen to inflate and deflate the dilation balloon(s) and at least one inflation lumen to inflate and deflate the retention balloons(s). It is contemplated that any of the inflation lumens included in the dilation device can serve as the tubular support for the dilation balloon(s) and the retention balloon(s). In other words, the tubular support may define the relevant inflation lumens.

The dilation device may have a continuous single pathway through its entirety to accommodate a guide wire. This pathway may include the inflation lumen for the dilation balloon, the retention balloon, and the tubular support; or it may be a separate lumen that is contained within the walls of an inflation lumen, the tubular support; or combinations thereof.

According to the present invention, the dilation device may be utilized in "inside-out" or "outside-in" dilation procedures. Inside-out dilation procedures involve attachment of the dilation device to the guide wire outside of the patient's mouth or inside the non-vascular lumen (e.g., the stomach or other space). A non-limiting example of attachment outside the patient's mouth may involve the following steps: insertion of an endoscope that extends from outside the mouth to inside the stomach; conventional placement of a guide wire through the skin, abdominal wall and stomach wall utilizing a needle; insertion of a standard endoscopic forceps or an endoscopic snare through the working channel of the endoscope; using the forceps or snare to grasp the guide wire portion that is in the stomach and then pulling the guide wire through the working channel of the endoscope and out of the patient's mouth (unlike current practice where the entire endoscope is removed from the patient); securely attaching the end of the dilation device that is closest to the dilation balloon (not the retention balloon portion of the dilation device) to the end of the guide wire that extends from the patient's mouth; pulling the guide wire and attached dilation device back through the working channel of the endoscope so that the dilation balloon exits the working channel into the stomach via the guide wire portion that remains outside the skin. An non-limiting example of attachment of the dilation device to the guide wire inside the patient's stomach may involve the following features and/or steps: the dilation device contains a fixture (magnet, hook, loop, snare, etc.) at the end that is closest to the dilation balloon (the side that enters the mouth first); the dilation device is pushed through the working channel of the endoscope so that the fixture exits the working channel; the fixture is attached under visualization of the endoscope by connecting the fixture to the guide wire (that was inserted through the needle); pulling the guide wire portion that remains outside the skin so that the dilation device pulls through the working channel and into the stomach. Regardless of the steps used to place the dilation device in the stomach, after placement in the stomach it is pulled into and partially through the needle tract so that at least a portion of the deflated dilation balloon extends through the abdominal tissue and the skin and the retention balloon resides in the stomach.

Outside-in dilation procedures differ from inside-out procedures in that they do not involve pulling a dilator into position through the body after removal of the endoscope or passing the dilation device through the working channel of the endoscope in order to position the dilation device in the stomach, nor is there any need to attach the dilation device to a guide wire that extends from the patient's stomach through the mouth. Outside-in procedures may involve the following steps: insertion of an endoscope that extends from outside the mouth to inside the stomach; conventional initial placement of a guide wire through the skin, abdominal wall, and stomach wall through an inserted needle and then removal of the needle; mounting the dilation device over the end of the guide wire that is outside of the patient's skin; partial insertion of the dilation device into the needle tract so that the retention balloon enters the stomach before any portion of the dilation balloon.

In positioning the dilation device, the dilation balloon and retention balloon must be in a deflated state so that the dilation device easily slides through the working channel of the endoscope and/or it penetrates the needle tract without excessive force. Preferably, the dilation device in this deflated state wraps and folds around the tubular support as much as possible to minimize the effective cross-sectional area of the dilation device during insertion through the endoscope and/or needle tract. Such folding and wrapping is achieved by intentionally folding the balloon walls in pre-planned arrangements, via the use of a pleater and/or folder manufacturing apparatus, or by random overlapping and folding afforded by the flexible nature and thinness of the balloon walls.

According to the invention, the dilation device has at least one retention balloon at the proximal portion of the device and at least one dilation balloon at the distal portion of the device. The proximal retention balloon(s) and dilation balloon(s) may be inflated independently. The dilation balloon has a length that is inflatable to a specified diameter and this length is placed in the needle tract. The dilation balloon inflates radially to provide an atraumatic dilation of the entire needle tract to create the stoma tract. The retention balloon is adjacent to the proximal section of the dilation balloon and is located placed inside the stomach. This retention balloon inflates to dimensions that are greater than the dilation balloon to stabilize the wall of the stomach during insertion of a catheter tube over the dilation portion of the device. The retention balloon also provides resistance against pulling forces in the distal direction of the device thereby helping to keep the dilation balloon from pulling out of the stoma tract during the procedure.

A better understanding of the above and many other features and advantages of the dilation device and/or dilation system may be obtained from a consideration of the detailed description of the invention below, particularly if such consideration is made in conjunction with the appended drawings.

BRIEF DESCRIPTION OF THE DRAWINGS

FIG. 1A is a side cross-sectional view illustrating an exemplary dilation device.

FIG. 2 is a side cross-sectional view illustrating a detail of an exemplary dilation device.

In FIG. 5A, the catheter or feeding tube is shown fitting over the fully or partially inflated dilation balloon through the dilated stoma tract and into the portion of the lumen stabilized by the inflated retention balloon. FIG. 5B illustrates the stoma dilation device deflated and at least a portion of the device being withdrawn through the catheter or feeding tube.

DETAILED DESCRIPTION

Figure 1B:
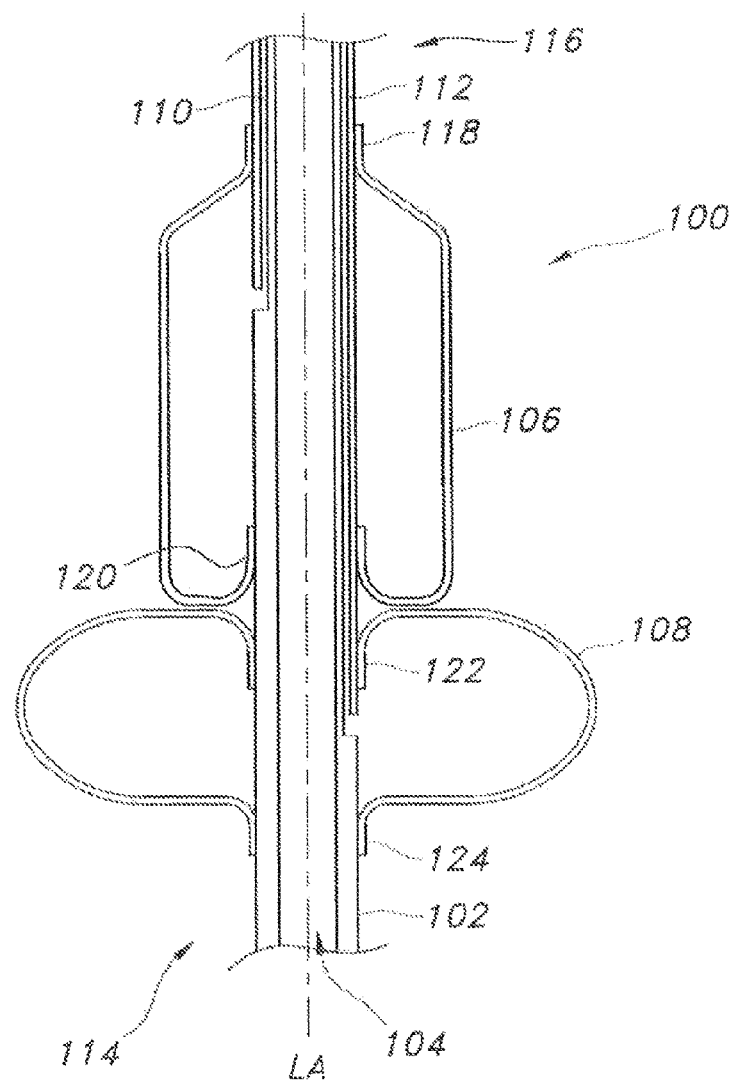
FIG. 1B is a side cross-sectional view illustrating another embodiment of the exemplary dilation device.

Reference will now be made in detail to one or more embodiments, examples of which are illustrated in the drawings. It should be understood that features illustrated or described as part of one embodiment may be used with another embodiment to yield still a further embodiment.

Turning now to the drawings, there is shown at FIGS. 1A and 1B in side, cross-sectional view, an exemplary stoma dilation device 100 that includes a tubular support 102 defining at least one continuous pathway 104 through the device. The continuous pathway is configured to accommodate a guide wire.

The tubular support 102 has a length, width and a longitudinal axis "LA". The tubular support 102 should be flexible but not too flexible as to readily collapse or kink when pressure is applied radially or axially. The width of the tubular support should be sufficiently small that it may fit in the working channel of an endoscope. For example, the tubular support may have a width of from about 0.2 to about 2 millimeters. More desirably, the tubular support may have a width of from about 0.5 to about 1.75 millimeters. The tubular support may be made of a variety of suitable materials. Exemplary materials include thermoplastic polyurethanes such as TECOFLEX® medical-grade aliphatic polyether polyurethanes available from Lubrizol Advanced Materials, Inc., Thermedics™ Polymer Products, Wilmington, Mass.

At least one inflatable dilation balloon 106 and at least one inflatable retention balloon 108 is located on the tubular support. Each retention and dilation balloon has at least one characteristic dimensional shape or "cross section" and at least one characteristic "diameter" that is referenced orthogonally to the longitudinal axis LA. The dilation balloon 106 has at least one dilation balloon inflation lumen 110 to inflate and deflate the dilation balloon. The retention balloon 108 has at least one retention balloon inflation lumen 112 to inflate and deflate the retention balloon. Desirably, the inflation lumens are integrated in the tubular support 102. In this regard, the tubular support 102 may define multiple lumens. That is, the tubular support may define a continuous pathway 104, at least one dilation balloon inflation lumen 110 to inflate and deflate one or more dilation balloons 106, and at least one retention balloon inflation lumen 112 to inflate and deflate one or more retention balloons 108. It is contemplated that the inflation lumens may be separated from the tubular support and be in the form of pilot tubes or the like.

Referring now to FIG. 2 of the drawings, there is illustrated in side cross-sectional view an alternative inflation lumen configuration. In this configuration, a single inflation lumen is separated or divided by a plug "P" into a one dilation balloon inflation lumen 110 and one retention balloon inflation lumen 112. In such a configuration, the dilation balloon may be inflated from the distal end of the device and retention balloon may be inflated from a proximal end of the device that may extend through an endoscope or other device.

Referring again to FIGS. 1A and 1B, the dilation device has a proximal end 114 and a distal end 116. Generally speaking, the inflatable dilation balloon 106 forms at least a first portion of the device and the inflatable retention balloon 108 forms at least a second portion of the device. For example, the dilation balloon 108 is located towards the distal end 116 and the retention balloon is located towards the proximal end 114.

According to the invention, the inflatable retention balloon 108 is configured to have an effective cross section upon full, unrestrained inflation that is greater than the largest cross section of the inflatable dilation balloon 106 upon inflation as is generally illustrated in FIGS. 1A and 1B. The dilation balloon(s) has a length and a circular cross section with a pre-determined diameter along the length upon full inflation to fit a specific sized catheter tube device. Alternatively, the dilation balloon(s) may be dilated to various effective diameters using respectively different inflation pressures to fit various catheter tubes. As a non-limiting example, the effective inflated diameter of the dilation balloon may range from about 3 to about 10 millimeters. As another non-limiting example, the effective inflated diameter of the dilation balloon may range from about 2 to about 8 millimeters. An inflated dilation balloon with a length and with a non-circular cross section along the length, e.g. elliptical or oval, is also contemplated.

The proximal section of the device (that portion of the dilation device that is positioned in the non-vascular lumen) incorporates at least one retention balloon (also referred to as the "proximal retention balloon") having a substantially larger cross section or diameter than any diameters of the dilation balloon(s). Generally speaking, the retention balloon may have a cross section or diameter that is about 1.5 times to about 3 times the diameter of the dilation balloon. Once this retention balloon is inflated, it functions to stabilize the wall of the lumen and/or provide retention of the dilation device within the non-vascular lumen (e.g., the stomach). The proximal retention balloon 108 may have a circular or a non-circular cross section as long as it is able to function as described above. The retention balloon may have or lack a cross section with one axis of symmetry. For example, the proximal retention balloon 108 may have a square, rectangular, triangular, elliptic, oval or other shape. Alternatively and/or additionally the proximal retention balloon 108 may incorporate lobes, fingers or projections that contribute to its overall cross-section so it is greater than the diameter of the dilation balloon 106.

Each balloon desirably includes two opposing open ends. The open ends may be attached to the tubular support. Referring to FIGS. 1A and 1B, the dilation balloon 106 may have open ends 118 and 120. The retention balloon 108 may have open ends 122 and 124. Desirably, the balloons are located as close together as possible. In this regard, as shown in FIG. 1A, the open end 122 of the retention balloon 108 may be inverted to provide a closer fit to the dilation balloon 106. It is contemplated that the open end 120 of the dilation balloon 106 may also be inverted to provide a close fit, as depicted in FIG. 1B.

The retention balloon component and the dilation balloon may be formed of materials such that the balloons are compliant, semi-compliant, or non-compliant. That is, the balloon may be relatively elastic (e.g., compliant) so that it stretches as well as expands upon inflation. The balloon may also be somewhat elastic (e.g., semi-compliant) so that it or expands but has limited stretch upon inflation. The balloon may be inelastic (e.g., non-compliant) so that it expands without significant stretch upon inflation. The balloons may each be made of a different material such that one may be compliant and one may be non-compliant. Various combinations are contemplated. Desirably, one or both of the balloons may be formed of polyurethane material identified as Pellethane® 2363-90A, available from Lubrizol Advanced Materials, Inc., Thermedics™ Polymer Products.

According to an aspect of the invention, the dilation devices includes a tubular support having a length, width and a longitudinal axis, the tubular support defining a continuous pathway through the device. The device further includes at least two inflatable balloons, at least a first balloon oriented axially on the tubular support forming a dilation region of the device and at least a second balloon forming a retention region defining a second portion of the device. At least one balloon inflation lumen is provided for each inflatable balloon such that the retention region is configured to have at least one effective cross section and/or diameter upon full, unrestrained inflation that is greater than the largest cross section and/or diameter of the dilation region upon inflation.

As illustrated in FIGS. 1A and 1B, the dilation balloon 106 is a first balloon oriented axially on the tubular support 102. The retention balloon 108 may desirably be oriented axially on the tubular support 102. However, other configurations are contemplated. For example, multiple retention balloons may be attached to the tubular support to project radially from the tubular support.

The present invention also covers a system for dilating a stoma and inserting a non-vascular catheter tube, the system includes a stoma dilation device as described above. The system also includes a non-vascular catheter tube configured to fit over the fully or partially inflated dilation balloon through the dilated stoma tract and into the portion of the non-vascular lumen stabilized by the retention balloon. According to the system, the stoma dilation device is configured to be deflated and at least a portion of the device withdrawn through the non-vascular catheter tube.

In an exemplary and non-limiting description of a placement of the device, an endoscope may be advanced into a non-vascular lumen (e.g., the stomach) to insufflate and allow palpation to locate a catheter tube location site (e.g., a PEG location site). Once the site is located, a needle may be inserted into the stomach through the abdomen and a guide wire may be introduced into the stomach through the needle.

Standard endoscopic forceps, an endoscopic snare, or a balloon attachment fixture may be inserted through the working channel of the endoscope. The forceps, snare or fixture is used to grasp the guide wire and the guide wire is pulled up through the working channel of the endoscope and out of the patient's mouth.

A dilation device with its attached inflation lumen is secured to the end of the guide wire and is pulled through the working channel of the endoscope using the guide wire and into the stomach. The dilation device may have a dilation balloon having a pre-determined volume and diameter upon full inflation and a retention balloon having a diameter upon full inflation that is greater than the largest diameter of the dilation balloon. When these balloons are in a folded or tightly wrapped state, the dilation device has an overall diameter that fits within the working channel of the endoscope. Typically, the diameter is in the range of about 2 millimeters or less.

Figure 3:
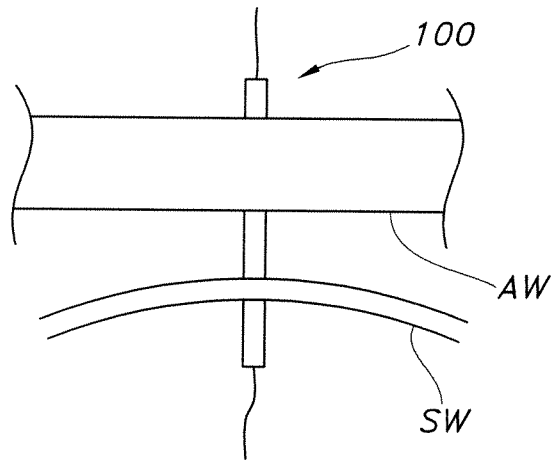
FIG. 3 is a side cross-sectional view illustrating the position of an exemplary dilation device pulled through the lumen wall and abdominal wall prior to inflation of the device.

The needle is removed from the stomach, while retaining the guide wire in the needle tract. The dilation device is pulled up into and partially through the needle tract so that it reaches the abdominal tissue and the skin on the exterior of the patient as illustrated in FIG. 3.

Figure 4A:
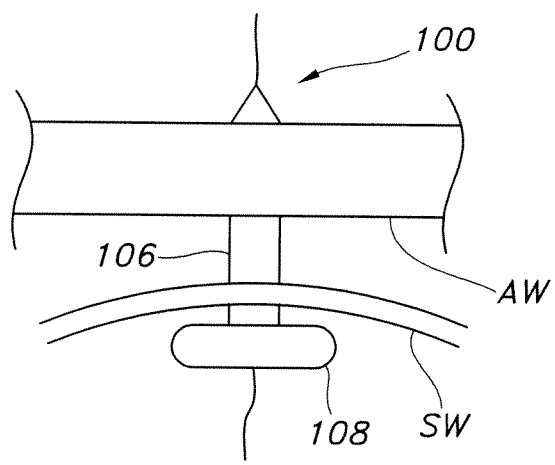
FIGS. 4A and 4B are side cross-sectional views an exemplary dilation device showing an inflated dilation balloon and inflated retention stabilizing the lumen wall against the abdominal wall.
Figure 4B:
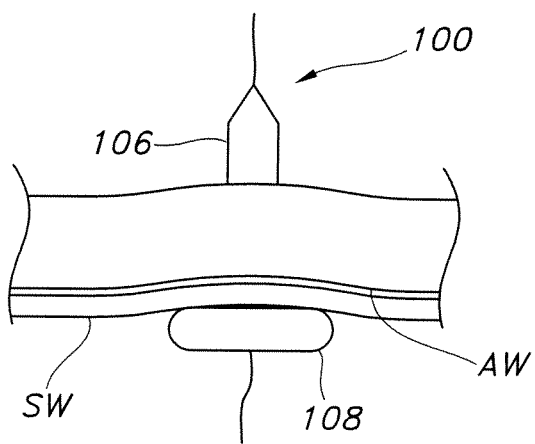

Referring now to FIGS. 4A and 4B, the dilation balloon 106 of the dilation device 100 is then inflated by gradually introducing controlled amounts of fluid (e.g., liquid or gas) to increase pressure in the balloon so it smoothly and gradually expands the needle tract into a stoma tract. The retention balloon 108 of the dilation device 100 is also then inflated by gradually introducing controlled amounts of fluid (e.g., liquid or gas) to increase pressure in the balloon so it smoothly and gradually expands. When the retention balloon 108 becomes larger than the dilation balloon 106 and expands to full inflation, it stabilizes the stomach wall "SW" by bringing it up against the wall of the abdomen "AW" as illustrated in FIG. 4B. According to an aspect of the invention, the fully inflated diameters of this balloon may be selected from a range to match the diameter of the catheter tube device (e.g., the PEG device) that will be inserted. The dilation device can have two different balloons in series; a dilation balloon (desirably non-compliant) that is positioned distally, and a separate retention balloon (that may also be non-compliant) that is positioned proximally. An example of a dilation device with a non-compliant balloon and a separate retention balloon has the separate retention balloon affixed to a proximal part of the dilation device to help retain the device in the patient's stomach and the non-compliant balloon, which is smaller than the separate retention balloon when both are fully inflated, is affixed distally and the non-compliant balloon is used to expand the needle tract into a stoma tract.

After the dilation device has its affixed balloons fully inflated, a peel-away sheath is placed over the distal-most portion of the dilation device (i.e., from the outside of the patient). The dilation balloon of the dilation device is partially deflated a small amount to allow the peel-away sheath to pass over the distal end of the dilation device and dilation balloon and through the stoma tract into the stomach.

Next, the dilation device has its balloons completely deflated. Because it is still attached to the guide wire, the dilation device may be removed through the working channel of the endoscope by withdrawing the guide wire through the working channel of the endoscope. Alternatively, the dilation device can be removed by cutting off the syringe inflation connector from the inflation lumen at the mouth (if such an inflation lumen is used) and pulled through the stoma site via the sheath. It is noted that the different inflation lumen configurations for the dilation device are illustrated in FIGS. 1A. 1B, and 2.

A catheter tube (e.g., a PEG device) is then threaded over the guide wire and the distal end of PEG device is inserted through the peel away sheath. The peel-away sheath is separated and removed from the stoma tract, any other placement tools are removed, and a retainer on the distal, in-dwelling end of the PEG device hold the PEG device in place.

Figure 5A:
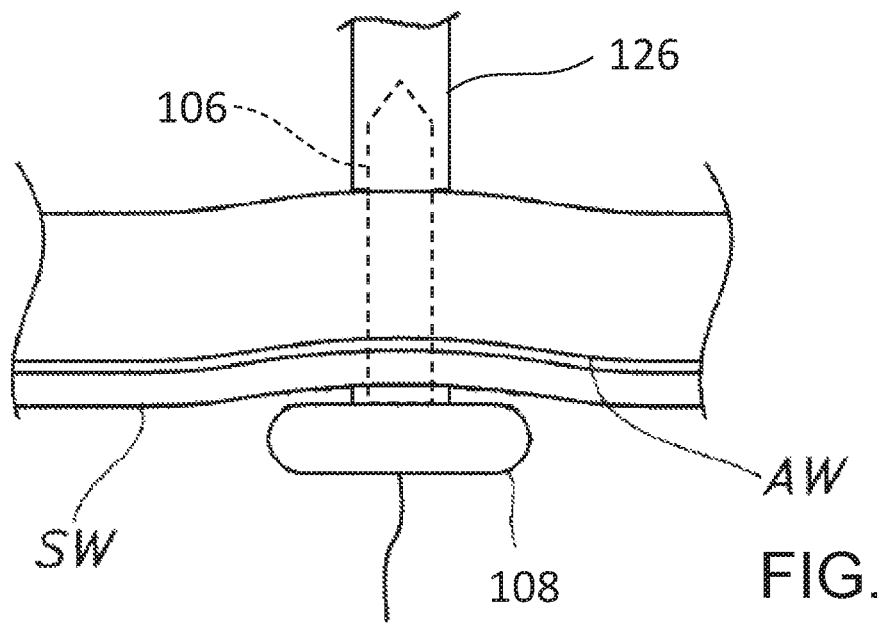
FIGS. 5A and 5B are side cross-sectional views of an exemplary catheter or feeding tube inserted through a dilated stoma tract in the lumen wall and abdominal wall.
Figure 5B:
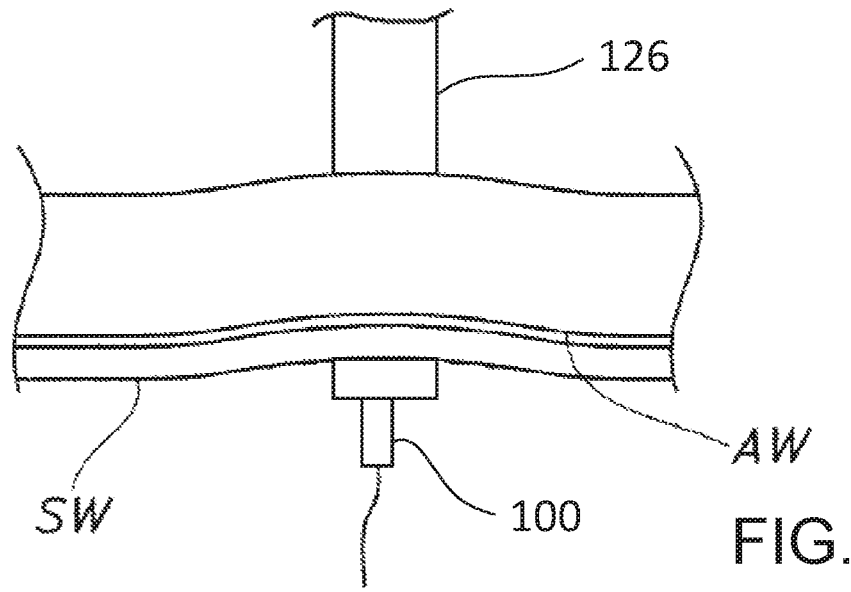

Alternatively, a catheter tube, such as a feeding tube, may be put into position without the use of a peel-away sheath. Referring to FIGS. 5A and 5B, after the dilation device 100 has its affixed balloons 106, 108 fully inflated, the dilation balloon 106 of the dilation device is deflated by only a small amount to allow the catheter or feeding tube 126 to pass over the distal end of the dilation device 100 and through the stoma tract into the stomach.

Next, the dilation device 100 has its balloon or balloons 106, 108 completely deflated. Because it is still attached to the guide wire, the dilation device 100 may be removed through the working channel of the endoscope by withdrawing the guide wire through the working channel of the endoscope. Alternatively, the dilation device 100 can be removed by cutting off the syringe inflation connector from the inflation lumen at the mouth (if such an inflation lumen is used) and pulled through the stoma site via the catheter tube 126. It is noted that the different inflation lumen configurations for the dilation device are illustrated in FIGS. 1A, 1B, and 2.

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

We claim:

1. A system for dilating a stoma to a gastric lumen and inserting a feeding tube, the system comprising:
    a stoma dilation device comprising:
        a tubular support having a length, width and a longitudinal axis, the tubular support defining a continuous pathway through the device;
        an inflatable dilation balloon located on the tubular support toward a distal end of the device, the dilation balloon being oriented axially on the tubular support for positioning the dilation balloon, within a needle tract to a gastric lumen, the inflatable dilation balloon configured to expand the needle tract into a stoma tract, the inflatable dilation balloon having an inflated cross-section ranging from 3 to 10 millimeters;
        a dilation balloon inflation lumen;
        an inflatable retention balloon located on the tubular support adjacent the dilation balloon, the retention balloon located at a proximal section of the device, the proximal section of the device positioned within the gastric lumen, the retention balloon having a diameter upon full, unrestrained inflation that is greater than the diameter of the dilation balloon upon inflation in order to stabilize a wall of the gastric lumen; and
        a retention balloon inflation lumen,
        the inflatable dilation balloon having two open ends attached to the tubular support and the inflatable retention balloon having two open ends attached to the tubular support,
        wherein one open end of the two open ends of the inflatable dilation balloon is adjacent one open end of the two open ends of the inflatable retention balloon and at least one of the adjacent open ends is inverted to position dilation balloon and the retention balloon close together; and
    a feeding tube configured to fit over the fully or partially inflated dilation balloon through the expanded needle tract and into the portion of the gastric lumen stabilized by the retention balloon, the feeding tube extending from skin at an exterior of a patient, through the needle tract, and into the gastric lumen to provide feeding solutions directly to the gastric lumen, wherein the stoma dilation device is configured to be deflated and at least a portion of the device withdrawn through the feeding tube.

2. The stoma dilation device of claim 1, wherein the inflatable retention balloon is configured to have a diameter upon full, unrestrained inflation that is 1.5 times to 3 times greater than the diameter of the inflatable dilation balloon upon inflation.

3. The stoma dilation device of claim 1, wherein the open end of the inflatable dilation balloon adjacent the open end of the inflatable retention balloon is inverted.

4. The stoma dilation device of claim 3, wherein the open end of the inflatable retention balloon adjacent the open end of the inflatable dilation balloon is inverted such that the adjacent open ends are both inverted.

5. The stoma dilation device of claim 1, wherein the open end of the inflatable retention balloon adjacent the open end of the inflatable dilation balloon is inverted.

6. The stoma dilation device of claim 5, wherein the open end of the inflatable dilation balloon adjacent the open end of the inflatable retention balloon is inverted such that the adjacent open ends are both inverted.

7. The stoma dilation device of claim 1, wherein inflatable dilation balloon and the inflatable retention balloon are each made of a different material.

8. The stoma dilation device of claim 1, further comprising an inflation lumen having a plug is positioned within the inflation lumen to define the dilation balloon inflation lumen and the retention balloon inflation lumen, the dilation balloon inflation lumen extending from the plug to a distal end of the device and the retention balloon inflation lumen extending from the plug to a proximal end of the device.

9. A stoma dilation device for expanding a needle tract to a gastric lumen into a stoma tract, the stoma dilation device comprising:
    a tubular support having a length, width and a longitudinal axis, the tubular support defining a continuous pathway through the device;
    at least two different inflatable balloons in series, at least a first balloon oriented axially on the tubular support and having two open ends attached to the tubular support forming a dilation region of the device for expanding a needle tract to a gastric lumen into a stoma tract, the first balloon having an inflated diameter ranging from 3 to 10 millimeters, and at least a second balloon having two open ends attached to the tubular support forming a retention region defining a second portion of the device;
    a balloon inflation lumen,
    wherein a plug is positioned between the first balloon and the second balloon within the balloon inflation lumen, the plug dividing the balloon inflation lumen to define a first balloon inflation lumen and a second balloon inflation lumen, the first balloon inflation lumen extending from the plug to a distal end of the device and the second balloon inflation lumen extending from the plug to a proximal end of the device, and
    wherein the retention region is configured to have a diameter upon full, unrestrained inflation that is 1.5 times to 3 times greater than the diameter of the dilation region upon inflation.

10. The stoma dilation device of claim 9, wherein at least one open end of the second balloon is inverted.

11. The stoma dilation device of claim 10, wherein the second balloon is oriented axially on the tubular support.

12. The stoma dilation device of claim 10, wherein one open end of the first balloon is adjacent one open end of the second balloon, and wherein the adjacent open ends are both inverted to provide a close fit between the first balloon and the second balloon.

13. A system for dilating a stoma to a gastric lumen and inserting a feeding tube, the system comprising:
    a stoma dilation device comprising:
        a tubular support having a length, width and a longitudinal axis, the tubular support defining a continuous pathway through the device;
        an inflatable dilation balloon located on the tubular support for dilating a stoma tract;
        a dilation balloon inflation lumen;
        an inflatable retention balloon located on the tubular support adjacent the dilation balloon, the retention balloon for stabilizing a portion of a gastric lumen in communication with the stoma tract; and
        a retention balloon inflation lumen; and
    a feeding tube configured to fit over the fully or partially inflated dilation balloon through the dilated stoma tract and into the portion of the gastric lumen stabilized by the retention balloon, the feeding tube extending from skin at an exterior of a patient, through the stoma tract, and into the gastric lumen to provide feeding solutions directly to the gastric lumen,
    wherein the stoma dilation device is configured to be deflated and at least a portion of the device withdrawn through the feeding tube.

14. The system of claim 13, wherein the retention balloon is oriented axially on the tubular support.

15. A system for dilating a stoma to a gastric lumen and inserting a feeding tube into the stoma, the system comprising:
    a stoma dilation device comprising:
        a tubular support having a length, width and a longitudinal axis, the tubular support defining a continuous pathway through the device;
        an inflatable dilation balloon located on the tubular support for dilating a stoma tract, the inflatable dilation balloon having an inflated diameter ranging from 3 to 10 millimeters;
        a dilation balloon inflation lumen;
        an inflatable retention balloon located on the tubular support adjacent the dilation balloon, the retention balloon being configured for stabilizing a portion of a gastric lumen in communication with the stoma tract by having a diameter upon full, unrestrained inflation that is greater than the inflated diameter of the dilation balloon in order to stabilize a wall of a lumen; and
        a retention balloon inflation lumen; and
    a feeding tube configured to fit over the fully or partially inflated dilation balloon through the dilated stoma tract and into the portion of the gastric lumen stabilized by the retention balloon, the feeding tube extending from skin at an exterior of a patient, through the stoma tract, and into the gastric lumen to provide feeding solutions directly to the gastric lumen,
    wherein the stoma dilation device is configured to be deflated and at least a portion of the device withdrawn through the feeding tube.

16. The system of claim 15, wherein the inflatable dilation balloon is oriented axially on the tubular support.

17. The system of claim 15, wherein the inflatable retention balloon is oriented axially on the tubular support.

18. The system of claim 15, wherein the inflatable retention balloon has two open ends attached to the tubular support and at least one open end is inverted.

19. The system of claim 15, wherein the inflatable retention balloon is configured to have a diameter upon full, unrestrained inflation that is 1.5 times to 3 times greater than the diameter of the inflatable dilation balloon upon inflation.

* * * * *